United States Patent [19]

Damhus et al.

[11] Patent Number: 5,688,757
[45] Date of Patent: Nov. 18, 1997

[54] SUGAR DERIVATIVES CONTAINING BOTH LONG AND SHORT CHAIN ACYL GROUPS AS BLEACH ACTIVATORS

[75] Inventors: Ture Damhus; Ole Kirk, both of København, Denmark; Frederick Edward Hardy, Newcastle-on-Tyne, Great Britain

[73] Assignees: Novo Nordisk A/S The Procter & Gamble Co., Bagsvaerd, Denmark; Novo Alle, Cincinnati, Ohio

[21] Appl. No.: 178,593

[22] Filed: Jan. 7, 1994

Related U.S. Application Data

[63] Continuation of Ser. No. 844,626, Mar. 30, 1992, abandoned.

[30] Foreign Application Priority Data

Jan. 22, 1990 [DK] Denmark .................... 0172/90

[51] Int. Cl.$^6$ .................... C11D 7/26; C11D 7/38; C11D 7/54
[52] U.S. Cl. .................... 510/376; 510/312; 510/470; 252/186.38; 252/186.39
[58] Field of Search .................... 252/95, 99, 186.38, 252/186.39; 510/312, 376, 470

[56] References Cited

U.S. PATENT DOCUMENTS

| | | | |
|---|---|---|---|
| 3,901,819 | 8/1975 | Nakagawa | 8/111 |
| 3,956,278 | 5/1976 | Prey | 536/119 |
| 4,283,301 | 8/1981 | Diehl | 252/102 |
| 4,412,934 | 11/1983 | Chung | 252/186.38 |
| 4,483,778 | 11/1984 | Thompson | 252/94 |
| 4,536,314 | 8/1985 | Hardy | 252/102 |
| 4,541,944 | 9/1985 | Sanderson | 252/95 |
| 4,797,300 | 1/1989 | Jandacek | 426/549 |
| 4,800,038 | 1/1989 | Broze et al. | 252/174 |
| 4,889,651 | 12/1989 | Broze | 252/95 |
| 4,943,563 | 7/1990 | Mutschler | 514/23 |
| 5,047,168 | 9/1991 | Broze et al. | 252/174 |
| 5,106,528 | 4/1992 | Francis | 252/186.23 |

FOREIGN PATENT DOCUMENTS

| | | | |
|---|---|---|---|
| 0068547 | 1/1983 | European Pat. Off. | 252/95 |
| 0185522 | 6/1986 | European Pat. Off. | |
| 0257700 | 3/1988 | European Pat. Off. | 252/99 |
| 0 325 100 | 7/1989 | European Pat. Off. | |
| 0 325 109 | 7/1989 | European Pat. Off. | |
| 0 325 124 | 7/1989 | European Pat. Off. | |
| 0 325 184 | 7/1989 | European Pat. Off. | |
| 89/01480 | 2/1989 | WIPO | |
| 90/08182 | 7/1990 | WIPO | |

OTHER PUBLICATIONS

Nishikawa, Y. et al. "Chemical and Biochemical Studies on Carbohydrate Esters II", *Chem. Pharm. Bull* 1976, 24(3), 387–93; *Chemical Abstracts*, vol. 84, p. 51, 173895h, 1976.

Nishikawa, Y., et al. "Chemical and Biochemical Studies on Carbohydrate Esters IV", *Chem. Pharm. Bull.*, 1977, 25(4), 624–631, *Chemical Abstracts*, vol. 88, pp. 619–620, 7220x, 1978.

Orbit Search Sve., File Japio, vol. 12, No. 358, p. 88, abstract of JP 63–112993 (Sep. 26, 1988).

*Primary Examiner*—Christine Skane
*Assistant Examiner*—Gregory R. Delcotto
*Attorney, Agent, or Firm*—Steve T. Zelson, Esq.; Elias J. Lambiris, Esq.

[57] ABSTRACT

Certain sugar derivatives have bleach-activating effect both on "hydrophilic" stains (e.g. tea or red wine) and on "hydrophobic" stains (e.g. grass or tomato sauce). The compounds in question are derivatives of pentoses or hexoses, having a long-chain acyl group and one or more short-chain acyl or aroyl groups attached through ester bonds. Optionally, a short-chain alkyl group is attached through a glycosidic bond. These compounds are non-toxic and biodegradable, and can conveniently be prepared by methods known in the art.

3 Claims, 5 Drawing Sheets

SUGAR DERIVATIVES CONTAINING BOTH LONG AND SHORT CHAIN ACYL GROUPS AS BLEACH ACTIVATORS

This application is a continuation application of co-pending application Ser. No. 07/844,626, filed Mar. 30, 1992.

TECHNICAL FIELD

This invention relates to a bleaching detergent composition, to a washing and bleaching liquor, and to a washing and bleaching process. More specifically, these comprise a hydrogen peroxide source and a bleach activator. The invention also relates to a compound for use as a bleach activator.

BACKGROUND ART

It is well known that detergents comprising peroxygen bleaches such as sodium perborate (PB) or sodium percarbonate (PC) are effective in removing stains from textiles. It is also known that the bleaching effect at temperatures below 50° C. can be increased by using a peracid precursor (bleach activator) such as tetraacetylethylenediamine (TAED), nonanoyloxybenzenesulfonate (NOBS, described in U.S. Pat. No. 4,412,934), 3,5,5-trimethylhexanoyloxybenzenesulfonate (ISONOBS, described in EP 120,591), or pentaacetylglucose (PAG), which is perhydrolyzed to form a peracid as the active bleaching species, leading to improved bleaching effect.

EP 325,100 proposes use of an acetylated sugar ether containing a long-chain alkyl group as a bleach activator. However, such compounds cannot be easily prepared.

It is the object of the invention to provide use of an improved bleach activator.

STATEMENT OF THE INVENTION

We have surprisingly found that certain sugar derivatives have bleach-activating effect both on "hydrophilic" stains (e.g. tea or red wine) and on "hydrophobic" stains (e.g. grass or tomato sauce). The compounds in question are derivatives of pentoses or hexoses, having a long-chain acyl group and one or more short-chain acyl or aroyl groups attached through ester bonds. Optionally, a short-chain alkyl group is attached through a glycosidic bond. These compounds are non-toxic and biodegradable, and can conveniently be prepared by methods known in the art.

Accordingly, the invention provides a bleaching detergent composition comprising a source of hydrogen peroxide and a compound of the general formula $$(A-CO-)(R'-CO-)_n X-R''_y \quad (I)$$

wherein
X is a pentose or hexose sugar moiety,
A—CO is a long-chain acyl group, whereby A is one of the following:

a $C_7$–$C_{19}$ straight-chain or branched, saturated or unsaturated hydrocarbyl,
$RO(CH_2-CH_2-O)_p-CH_2-$,
$RO(CH_2-CH_2-O)_p-$,
$ROOC-CH_2-CH_2-$,
$ROOC-CH=CH-$,
$RCOO-CH_2-$,
$RCONH(CH_2)_q-$ or $RNHCO(CH_2)_r-$,
whereby:
R is $C_8$–$C_{12}$ hydrocarbyl,
p is 0, 1, 2 or 3,
q is 1–5,
r is 2–4,
R'—CO is a $C_2$–$C_7$ short-chain acyl or aroyl group,
R" is a $C_1$–$C_4$ alkyl group,
y is 0 or 1, and
n is 1, 2, 3 or 4,
whereby
the alkyl group R" (if present) is attached through a glycosidic bond to the anomeric C atom, and the acyl groups are attached through ester bonds.

It follows from the number of available OH groups in the sugar molecule that n+y cannot exceed 3 for a pentose and 4 for a hexose.

The invention also provides a washing and bleaching liquor comprising a hydrogen peroxide source and the above-described compound of formula (I), and a washing and bleaching process in the presence of these.

Further, the invention provides novel compounds of formula (I). One aspect provides such compounds wherein n+y is 3 or less. These compounds are novel, whereas some hexose derivatives of formula (I) substituted at all OH groups (i.e. n+y=4) are known (e.g. JP-A 63-112,993).

Another aspect provides compounds of formula (i) wherein the long-chain acyl group excludes straight-chain saturated $C_8$ and $C_{12}$–$C_{20}$ acyl and wherein it is attached to the anomeric C atom. These compounds are novel and are particularly effective in the bleaching of hydrophobic stains.

DETAILED DESCRIPTION OF THE INVENTION

Hydromen Peroxide Source

The invention uses a hydrogen peroxide source as a bleaching agent, i.e. a compound that provides hydrogen peroxide in an aqueous detergent solution. Examples are hydrogen peroxide itself, perborates such as sodium perborates and percarbonates such as sodium percarbonate.

Sugar Derivative

The sugar derivatives according to the invention consist of a pentose or hexose sugar moiety, substituted with a long-chain acyl group and one or more short-chain acyl or aroyl groups through ester bonds, and optionally substituted with a short-chain alkyl group through a glycosidic bond.

These sugar derivatives may be prepared by methods known in the art. Reference is made to WO 89/01480; D. Plusquellec et al., Tetrahedron, Vol. 42, pp. 2457–2467, 1986; D. Plusquellec, Tetrahedron Letters, Vol. 28, No. 33, pp. 3809–3812, 1987; J. M. Williams et al., Tetrahedron, 1967, Vol. 23, pp. 1369–1378; W. J. Hennen et al., J.Org. Chem., Vol. 53, pp. 4939–4945 (1988); A. H. Haines, Adv. Carbohydr. Chem., Vol. 33, pp. 11–51, 1976; K. Yoshimoto et al., Chem. Pharm. Bull., 27 (11), 2661–2674 (1979); and Z. Györgydeàk et al., Liebigs Ann. Chem., 1987, pp. 235–241. In cases where these methods lead to mixtures of isomers, these may, if so desired, be separated, e.g. by chromatography on silica gel.

The long-chain fatty acyl group may be saturated, mono- or poly-unsaturated; straight-chain or branched-chain, preferably $C_8$–$C_{18}$. Some preferred acyl groups are octanoyl, nonanoyl, decanoyl, undecanoyl, dodecanoyl, tetradecanoyl, hexadecanoyl, octadecanoyl, 10-undecenoyl, oleoyl, 2-ethyl-hexanoyl, and 3,5,5-trimethyl-hexanoyl. $C_8$–$C_{12}$ hydrocarbyl groups are particularly preferred as they provide good bleach activation on hydrophobic stains.

The short-chain acyl or aroyl group is preferably a $C_2$–$C_6$ acyl group (especially acetyl) or benzoyl. Such derivatives can be prepared conveniently and economically.

The sugar moiety may be an aldohexose or aldopentose. For reasons of economy, glucose or xylose derivatives are preferred.

Alternatively, the sugar moiety may be a ketohexose or ketopentose. For reasons of economy, fructose derivatives are preferred.

In the case of glycoside esters (y=1), those with methyl or ethyl as the alkyl group R" may be preferred as they provide good surfactant properties. The glycoside bond may be in the α- or β-anomeric form.

Among the sugar esters (y=0), compounds having one of the acyl-groups attached to the anomeric C-atom (the 1-position of an aldose or the 2-position of a ketose) are preferred as they are most rapidly perhydrolyzed. This acyl group may be in the α- or β-anomeric position. Sugar esters having a long-chain acyl group (as specified above) attached to the anomeric C-atom are preferred, as they are particularly efficient for bleaching hydrophobic stains. Alternatively, sugar esters having a short-chain acyl group (e.g. an acetyl group) attached to the anomeric C-atom may be preferred, as they are particularly efficient for bleaching hydrophilic stains.

The sugar derivatives may be in the pyranose or furanose form.

It follows from the above that the number n+y+1 of acyl and alkyl substituents in the sugar molecule may vary from 2 up to 4 for a pentose or up to 5 for a hexose. Derivatives with only 2 or 3 substituents (n+y=1 or 2) may be preferred as they are more hydrophilic than those more fully substituted and are therefore more easily dissolved and may furthermore be more efficient as surfactants.

Alternatively, it may be preferred to use fully substituted compounds (n+y=3 for a penrose or 4 for a hexose), as these provide the maximum amount of peracid.

Sugar derivatives with the long-chain acyl group attached to a side chain of the sugar molecule (i.e. to the 6-position of glucose or the 1- or 6-position of fructose) may be preferred when a relatively slow release of the long-chain peracid is desired, so as to retain a suffactant effect, while short-chain peracid still may be formed rapidly by perhydrolysis in other positions of the molecule.

To ensure good stability, the bleaching detergent composition of the invention will generally be provided in particulate form. Preferably, the sugar derivative of formula (I) should be present in crystalline form, and for good crystallization it is preferable to use the sugar derivative in pure form rather than a mixture of isomers. For compounds substituted at the anomeric C atom this implies use of either the α- or the β-form rather than a mixture of these.

Some preferred compounds are 2,3,4,6-tetra-O-acetyl-1-O-(long-chain acyl)-glucose in α- or β-form where the long-chain acyl is one of the following: octanoyl, nonanoyl, decanoyl, undecanoyl, dodecanoyl, 10-undecenoyl, 3,5,5-trimethylhexanoyl or 2-ethylhexanoyl.

Bleaching Detergent Composition

The peroxide bleach and the sugar derivative (bleach activator) are preferably mixed in a molar ratio of 1:10 to 20:1, preferably 1:1 to 10:1.

The amount of peroxide bleach in the composition is preferably 1–90% by weight, most preferably 5–20% (as PB monohydrate). The amount of bleach activator is preferably 2–90%, e.g. 2–50%, especially 5–30% (percentages by weight).

Many of the sugar derivatives used in the invention are effective as non-ionic surfactants. In addition, the composition of the invention may comprise other surfactants, e.g. of the non-ionic and/or anionic type. Examples of nonionics are alcohol ethoxylates (AE), nonylphenol ethoxylates, alkyl polyglycosides (APG), and monoesters of carbohydrates (e.g. of free sugars or of glycosides). Examples of anionics are linear alkylbenzene sulfonates (LAS), fatty alcohol sulfates, fatty alcohol ether sulfates (AES), α-olefin sulfonates (AOS) and soaps.

Further, the composition of the invention may contain other conventional detergent ingredients such as suds-controlling agents, foaming boosters, chelating agents, ion exchangers, alkalis, builders, cobuilders, other bleaching agents, bleach stabilizers, fabric softeners, anti-redeposition agents, enzymes, optical brighteners, anti-corrosion agents, fragrances, dye-stuffs, blueing agents, formulation aids, fillers and water.

The composition of the invention may be provided in liquid form or in powder or granular form. It may be formulated in analogy with the frame formulations for powder detergents given at p. 288 of J. Falbe: Surfactants in Consumer Products. Theory, Technology and Application, Springer-Verlag 1987 by replacing all or part (e.g. 50%) of the non-ionic surfactant with ester according to the invention.

Washing and Bleaching Liquor

The washing liquor of the invention can be obtained by dissolving the above-described detergent in water, or the ingredients can be added and dissolved separately. Typically, the total detergent concentration will be 1–20 g/l, the amount of the hydrogen peroxide source will be 0.05–5 g/l, especially 0.25–1 g/l (calculated as sodium perborate monohydrate), and the amount of the sugar derivative will be 0.1–2.5 g/l, especially 0.25–1.5 g/l.

Washing and Bleaching Process

The washing process of the invention is typically carried out with the above-described liquor at temperatures of 20°–60° C. for 10–60 minutes in a conventional washing machine.

EXAMPLES

Figure 1:
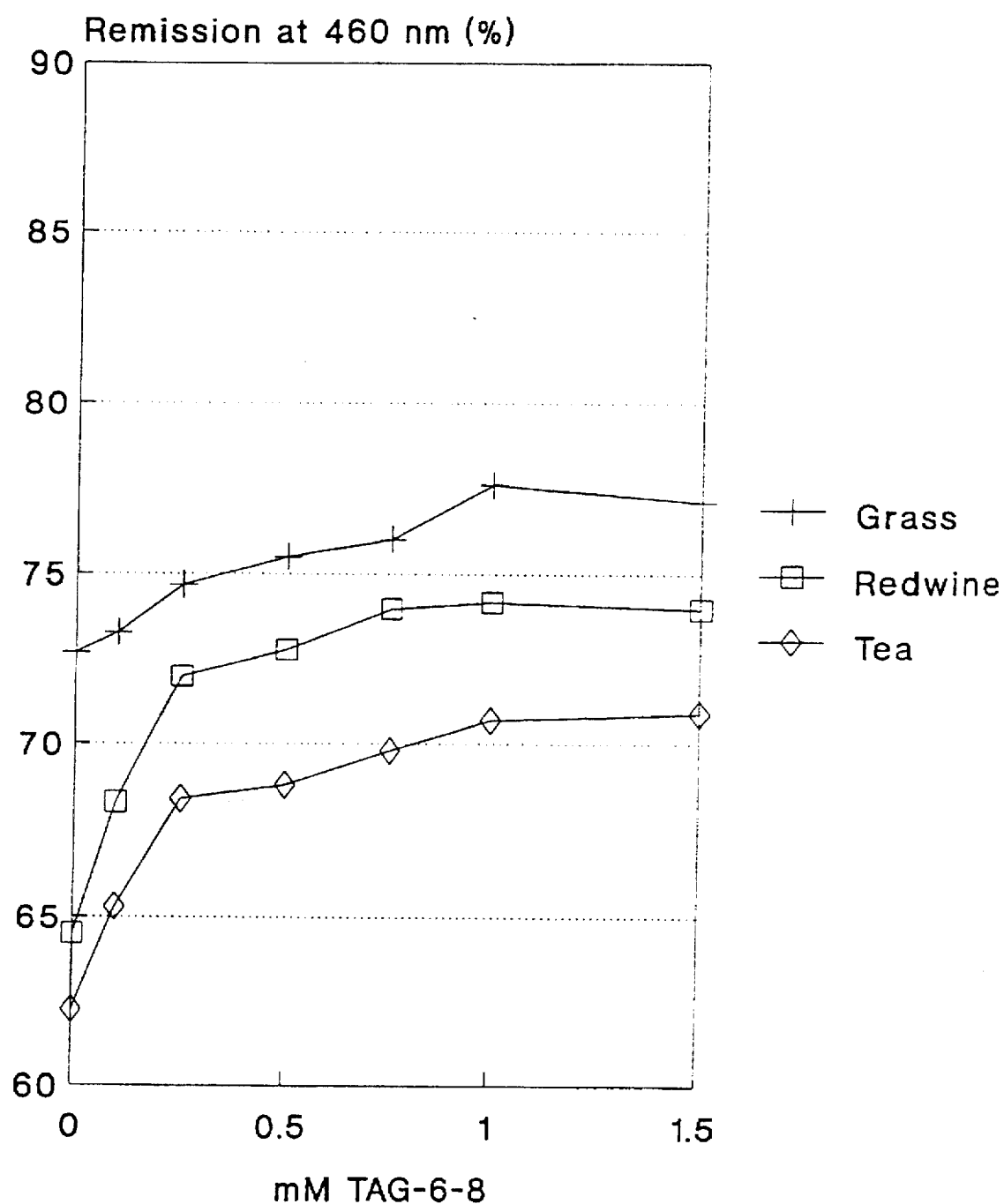
FIGS. 1–3 and 5 show bleach activation at varying concentrations of three different sugar derivatives according to the invention on three different soilings.

The preparations of the sugar derivatives were generally mixtures of the α- and β-anomers. In all cases satisfactory $^1$H-NMR spectra were obtained for the preparations. The preparations were all approximately 90% pure, but were dosed in the bleaching experiments as if 100% pure.

Unless otherwise stated, the inventive sugar derivatives were added to the various test-solutions as either methanol or ethanol solutions, while TAED, PAG, and ISONOBS were added directly. It has been checked that methanol/-ethanol at the levels attained by adding the sugar derivatives in this way have no influence in the experiments performed.

Example 1

This example is concerned with an examination of glucose ester and glycoside ester preparations as activators for hydrogen peroxide in the bleaching of test swatches soiled with tea, red wine, or grass.

The test swatches used were prepared by homogeneously soiling cotton cloth with tea, red wine, or grass juice, and then air-drying the soiled cloth overnight in the dark. The resulting material was stored in the dark at 4° C. (tea, red wine) or below 0° C. (grass) for at least 2 weeks before cutting test swatches.

The experiments were carried out as small-scale analogues of a Terg-o-tometer washing trial, i.e. isothermally in a series of beakers with concerted stirring (and alternating stirring direction). The soiled textile was loaded to 9 g/l washing liquor.

The washing liquor employed was a 50 mM sodium carbonate buffer at pH 10.5 with 0.4 g nonionic surfactant/l added (the preparation Berol 160 from Berol Nobel was used, a $C_{12}$–$C_{14}$ fatty alcohol ethoxylate with an EO value of 6). The washing liquor was prepared from demineralized water.

Washing temperature was 40° C.

Duration: 30 min.

After washing, the swatches were rinsed thoroughly in tap water and then air-dried in the dark overnight.

Evaluation of the bleaching effects was carried out by measuring the remission at 460 nm of unfiltered light, using a Datacolor Elrephometer 2000.

In Table 1 below, preparation 1 is 1-O-acetyl-6-O-octanoylglucose, while preparations 2 and 3 are 2-O-acetyl and 3-O-acetyl derivatives of ethyl 6-O-decanoylglucopyranoside, respectively.

TABLE 1

| Clean textile | Remission at 460 nm (%) 85 | | |
|---|---|---|---|
| | Red wine | Tea | Grass |
| 0. Soiled, not washed | 46 | 50 | 43 |
| 1. Reference (washing liquor alone) | 53 | 50 | 70 |
| 2. 10 mM $H_2O_2$ washing liquor | 67 | 66 | 75 |
| 3. As 2 + 2 mM prepn. 1 | 75 | 74 | 81 |
| 4. As 2 + 2 mM prepn. 2 | 71 | 69 | 80 |
| 5. As 2 + 2 mM prepn. 3 | 71 | 70 | 79 |
| 6. As 2 + 1 mM TAED | 74 | 72 | 76 |

The activator TAED (tetraacetylethylenediamine) was used for a comparison and was dosed to 1 mM, since it possesses 2 perhydrolyzable acetyl groups.

Standard deviations were in all cases below 1 remission unit. The three sugar derivative preparations thus all show benefits compared to using $H_2O_2$ alone; all are superior to TAED in removing grass stains; and preparation 1 is superior to TAED on tea and red wine as well.

Example 2

This example is concerned with an examination of some further sugar derivative preparations as activators for hydrogen peroxide. The experimental setup was as described in Example 1.

In Table 2 below, preparation 4 is 1-O-acetyl-6-O-decanoylglucose, preparation 5 is 2,3,4-tri-O-acetyl-6-O-octanoyl-glucose while preparations 6 and 7 are 2,3-di-O-acetyl and 2,3,4-tri-O-acetyl derivatives of ethyl 6-O-decanoylglucopyranoside, respectively.

The sugar derivative preparations were dosed to 2 mM except preparations 6 and 7 which were dosed in the same weight amount as preparations 2 and 3 in Table 1. The results are shown in Table 2.

TABLE 2

| Clean textile | Remission at 460 nm (%) 85 | | |
|---|---|---|---|
| | Red wine | Tea | Grass |
| 0. Soiled, not washed | 46 | 50 | 43 |
| 1. Reference (washing liquor alone) | 53 | 50 | 70 |
| 2. 10 mM $H_2O_2$ in washing liquor | 67 | 64 | 74 |
| 3. As 2 + 2 mM prepn. 4 | 74 | 70 | 84 |
| 4. As 2 + 2 mM prepn. 5 | 74 | 70 | 73 |
| 5. As 2 + 0.08% prepn. 6 | 74 | 69 | 78 |
| 6. As 2 + 0.08% prepn. 7 | 72 | 69 | 75 |

Standard deviations are as in Example 1, and we may thus again conclude that all the preparations give significant benefits as activators at the level tested.

Example 3

With the experimental setup from Example 1, preparations of 1-O-acetyl-6-O-acylglucose with acyl=octanoyl, decanoyl, dodecanoyl, tetradecanoyl, and hexadecanoyl were tested.

The following remission values at 460 nm (%) were obtained.

| | Ref. | $C_8$ | $C_{10}$ | $C_{12}$ | $C_{14}$ | $C_{16}$ |
|---|---|---|---|---|---|---|
| Red-wine swatches | 66.5 | 74.7 | 74.8 | 74.3 | 72.6 | 72.6 |
| Tea swatches | 64.0 | 70.7 | 70.3 | 70.8 | 68.6 | 68.6 |
| Grass swatches | 73.7 | 81.1 | 84.1 | 77.5 | 66.7 | 55.0 |

The reference value, as in Example 1, was obtained with the washing liquor alone. Analogous bleaching trials with no background nonionic surfactant gave the following remission values at 460 nm (%).

| | Ref. | $C_8$ | $C_{10}$ | $C_{12}$ | $C_{14}$ | $C_{16}$ |
|---|---|---|---|---|---|---|
| Red-wine swatches | 65.0 | 74.7 | 75.4 | 73.4 | 72.2 | 72.7 |
| Tea swatches | 61.8 | 71.0 | 71.0 | 69.1 | 68.6 | 68.7 |
| Grass swatches | 47.9 | 63.3 | 83.5 | 64.9 | 54.8 | 51.6 |

Quite clearly, under both sets of conditions, there is an optimum stain removal at chain length 10. With no nonionic present, all five inventive compounds provide benefits on each of the three stains. With AE present, the same overall picture is obtained for red-wine and tea stains as without AE, but the background removal of grass is so large that only the $C_8$ and $C_{10}$ compounds provide substantial further removal (and the $C_{14}$ and $C_{16}$ compound even interfere negatively with the alcohol ethoxylate).

Example 4

In this example the hydrogen peroxide activating effect of the fully acylated compound 1,2,3,4-tetra-O-acetyl-6-O- octanoylglucose (TAG-6-8, for short) was monitored by the amount of peracid formed in a model washing liquor (peracid formation may be monitored for example by iodometry at 5° C. as described by Sully and Williams in *Analyst*, 1962, 67, 653).

The experimental conditions were: 10 mM $H_2O_2$ in 50 mM sodium carbonate buffer (prepared from demineralized water) at pH 10.5 with 0.4 g nonionic surfactant/l added (the preparation Berol 160 from Berol Nobel was used, a $C_{12}$–$C_{14}$ fatty alcohol ethoxylate with an EO value of 6). TAG-6-8 was dosed to a level of 2 mM. The results are shown in Table 3:

TABLE 3

| Time (min) | Peracid (mM) |
|---|---|
| 3 | 3.0 |
| 15 | 2.7 |

The above data show that TAG-6-8 should be a very efficient activator for peroxide compounds since 3 mM peracid is formed in only 3 minutes from a 2 mM solution of TAG-6-8.

Example 5

Figure 2:
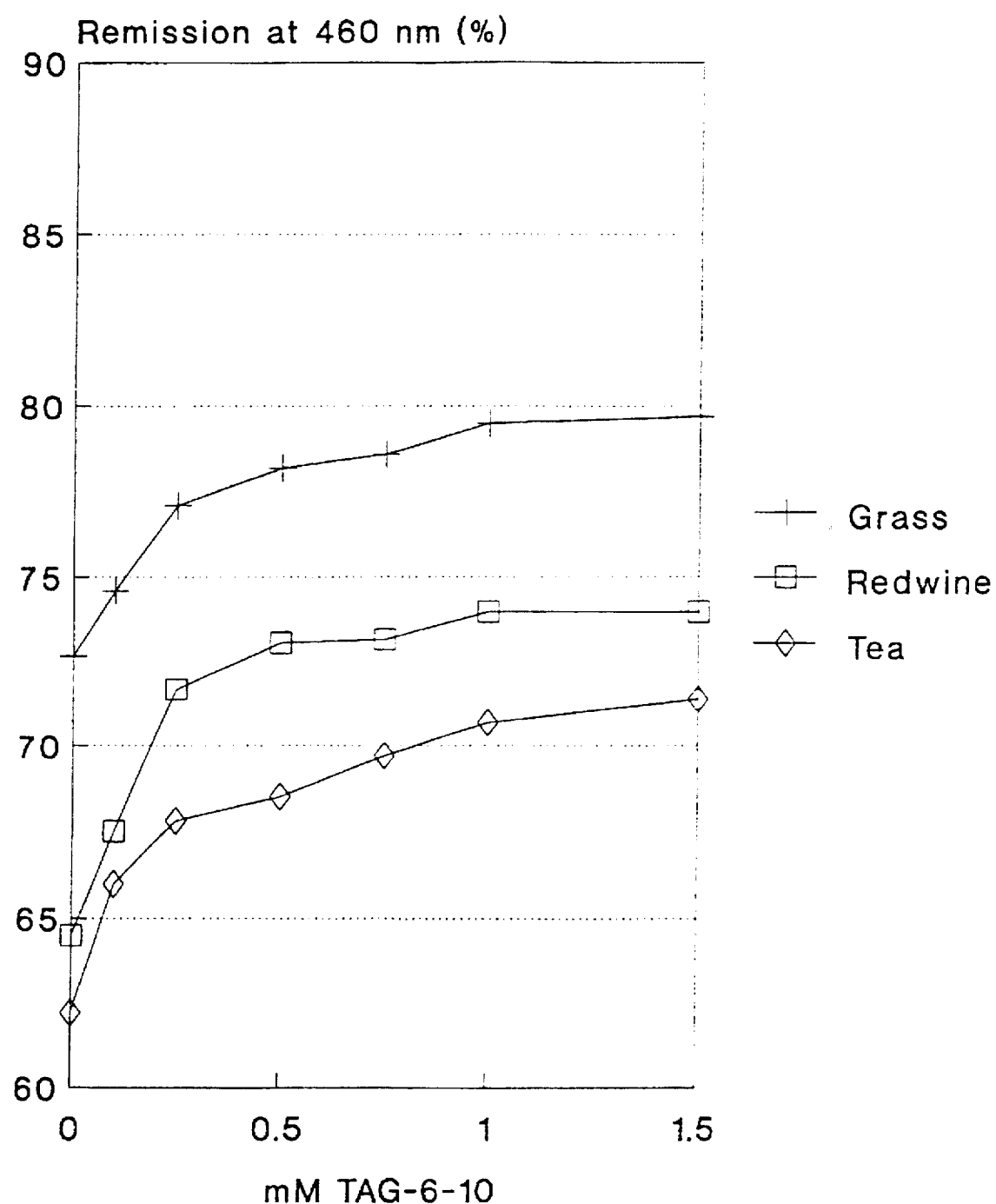

The fully acylated compounds TAG-6-8=1,2,3,4-tetra-O-acetyl-6-O-octanoylglucose and TAG-6-10, the corresponding decanoyl derivative, were subjected to a study of effect versus increasing dosage, again under the small-scale washing conditions described in Example 1. The hydrogen peroxide concentration was kept constant at 10 mM while varying the activator concentration. FIGS. 1 and 2 graph the results. Indeed, TAG-6-8, also presented in Example 4 for its peracid formation, bleaches the hydrophobic as well as the hydrophilic stains. Like with the monoacetylated compounds in Example 3, the $C_8$ and $C_{10}$ compounds here behave more or less identically on red-wine and tea stains, while the C10 compound is clearly superior on grass.

Figure 3:
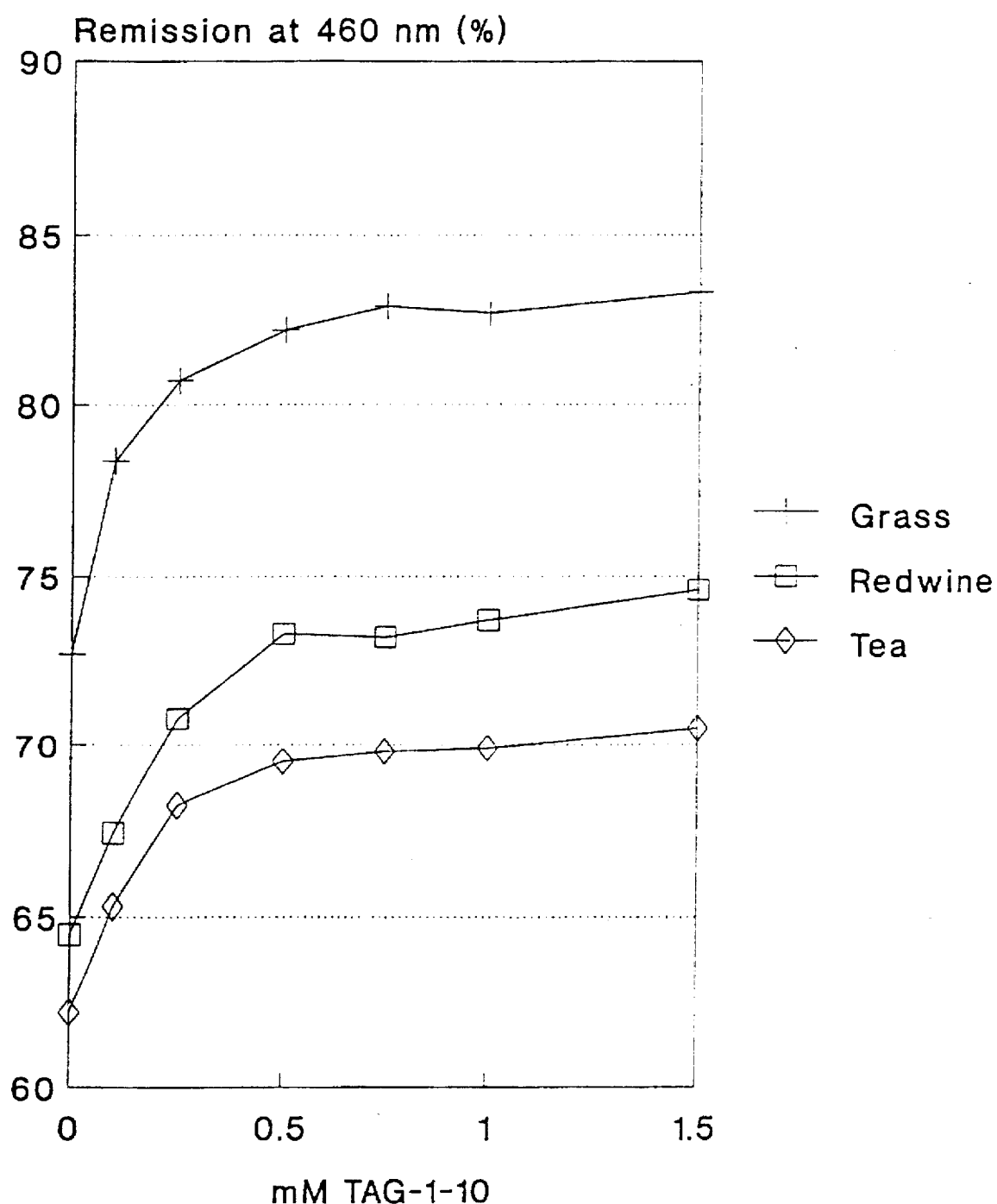
Figure 5:
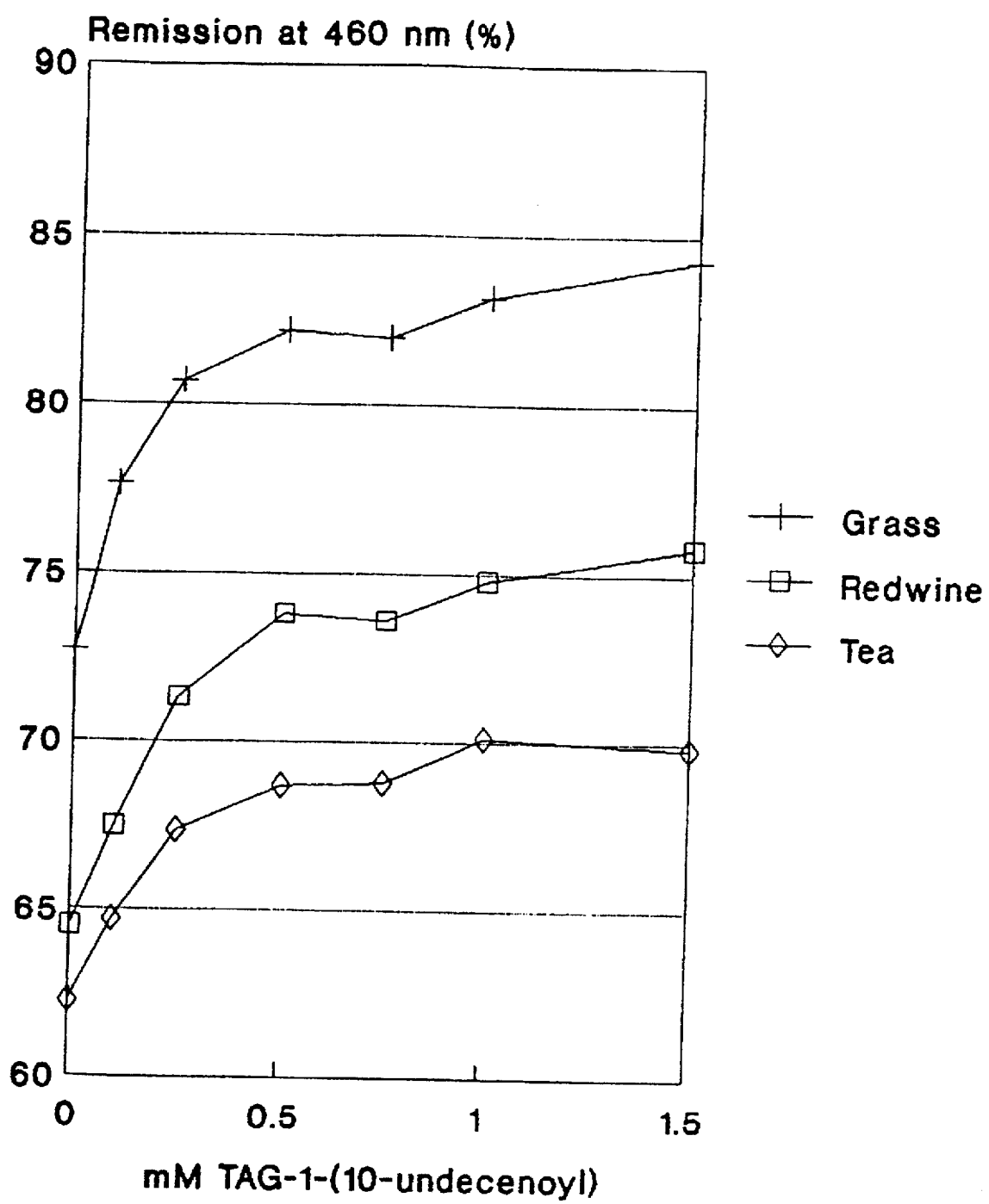

For the compounds TAG-1-10=2,3,4,6-tetra-O-acetyl-1-O-decanoyl-glucose (as a preparation with more than 95% α-anomer) and TAG-1-(10-undecenoyl)=2,3,4,6-tetra-O-acetyl-1-O-(10-undecenoyl)glucose (α:β ratio approx. 7:3) dose-effect studies analogous to the above ones are presented in FIGS. 3 and 5. It is seen that with the long-chain acyl placed at the anomeric carbon, an even better effect-is obtained on the hydrophobic stain, i.e., grass, in comparison with the TAG-6 compounds, while maintaining significant effects on the hydrophilic stains. The two TAG-1 compounds behave very similarly.

Figure 4:
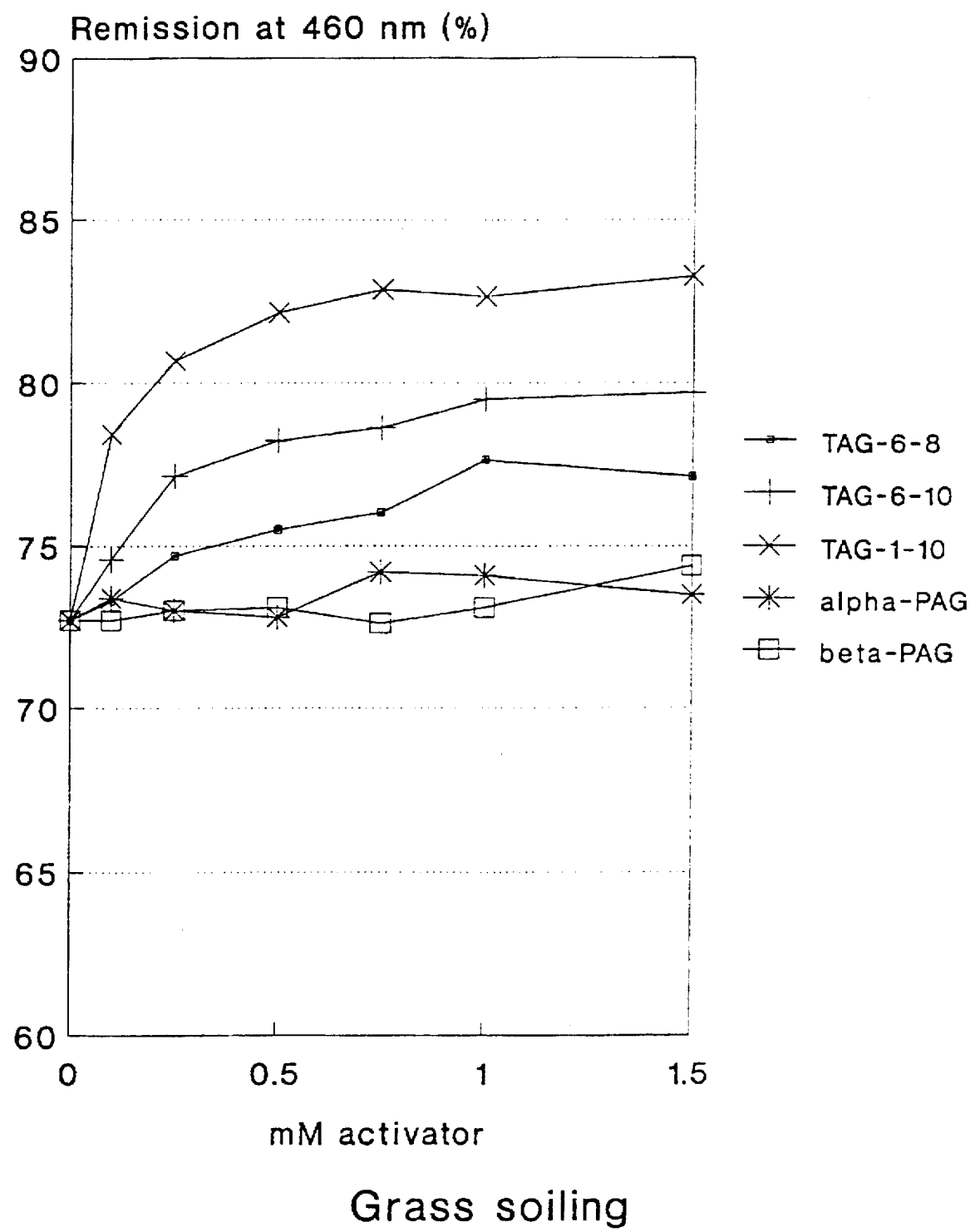
FIG. 4 shows a similar comparison of three sugar derivatives according to the invention and two prior-art bleach activators. Details are given in Example 5.

Finally, in FIG. 4 a comparison is made between the bleaching behavior on grass soiling of three of the TAG-fatty acyl compounds and the reference activator PAG (pentaacetylglucose), the most closely related compound within the prior art. It is seen that on this soiling, a significant improvement results from the substitution of one acetyl group by a long-chain acyl group, whether in the 1- or the 6-position.

Example 6

This example compares the bleaching efficacy of a wash liquor containing 2,3,4,6 tetra-O-acetyl-1-O-decanoylglucose (TAG-1-10), a derivative in accordance with the present invention, with that of a wash liquor containing each of several prior art bleach activators, viz. sodium 3,5,5-trimethylhexanoyloxyben-zenesulfonate (ISONOBS), pentaacetylglucose (PAG) and tetraacetylethylene-diamine (TAED).

The test was carried out in Launder-o-Meter pots each of which contained 500 mls of a wash liquor at 40° C. in water of 18° Clark hardness (Ca:Mg=3:1). The wash liquor contained 1% by weight of a detergent composition comprising (in weight percent).

| | |
|---|---|
| Linear Sodium $C_{11.8}$ alkylbenzenesulfonate | 5.9 |
| Sodium Tallow alkyl sulfate | 2.55 |
| Sodium silicate ($SiO_2$:$Na_2O$ = 1.6:1) | 2.9 |
| Magnesium sulfate | 0.4 |
| Polyacrylic acid | 3.9 |
| EDTA (ethylenediaminetetraacetic acid) | 0.25 |
| CMC (carboxymethylcellulose) | 0.3 |
| EDTMP* | 0.3 |
| Sodium sulfate | 10.7 |
| Zeolite A | 20.5 |
| Dobanol 45E7 nonionic | 5.4 |
| Sodium carbonate | 9.8 |
| Suds suppressor | 4.0 |
| Sodium perborate tetrahydrate | 20.0 |
| Bleach activator | 5.0** |

*EDTMP = ethylenediaminetetrakis(methylenephosphonic acid)
**Except PAG which was 4.0 parts Thus, the wash liquor was 1.0 mM with respect to PAG and TAG-1-10, and TAED and ISONOBS were present in the detergent in equal weight amounts as TAG-1-10.

The wash liquor was prepared as a stock solution of all of the components except the perborate bleach and activator which were added as weighed amounts into the pot immediately before the test commenced. The TAG-1-10 (as a preparation with an α:β anomer ratio of approx. 3:1 ) was added directly into the pot containing the wash liquor and dispersed using a high speed mixer. Each pot was loaded with a series of circular cotton fabric swatches soiled with tea, wine, paprika and tomato stains. The tea and wine stains were used to evaluate hydrophilic stain bleaching and were judged instrumentally by a Hunter Colour Reflectance Meter. The paprika and tomato stains were used to assess hydrophobic stain removal and were assessed visually by an expert panel using a paired comparison technique. The panellists' preferences are expressed in Panel Score Units (P.S.U.) on 1-5 Scheffe scale.

Results are shown below, normalised in each case to ISONOBS as 0. ISONOBS was chosen for this purpose as it generates a water soluble peroxyacid bleach that has both hydrophilic and hydrophobic stain removal capability. The figures in parentheses are the yardsticks at the 95% confidence level.

| | DELTA L | | P.S.U. | |
|---|---|---|---|---|
| | Tea | Wine | Paprika | Tomato |
| ISONOBS | 0 | 0 | 0 | 0 |
| PAG | 1.6 (1.4) | 0.5 (1.0) | −1.8 (0.9) | −3.6 (0.7) |
| TAED | 2.8 (1.6) | 0.7 (1.2) | −1.6 (1.0) | −4.0 (0.1) |
| TAG-1-10 | 1.8 (1.9) | 1.0 (0.6) | 0.6 (1.6) | 0.3 (0.6) |

It can be seen that, on hydrophilic stains, TAG-1-10 provides equivalent overall bleaching to PAG and TAED and, whilst not significantly better than ISONOBS on tea stains, it is significantly better on wine stains. On hydrophobic stains TAED and PAG give significantly poorer stain removal than ISONOBS whilst TAG.-1-10 is at least as good as ISONOBS.

Example 7

This example compares the stain removal performance of TAG-1-10 (see preceeding example), pentaacetylglucose (PAG) and tetraacetylethylene-diamine (TAED) in a split bundle washing trial in domestic washing machines.

The test employed Miele (Model W756) Washing Machines employing 105 g of a detergent product in a 60° C. mainwash cycle with 11 liters of water (city water of a hardness of approx. 12° dH). Each machine was loaded with 18.1 kg of normally soiled domestic fabrics (shirts, tea towels (dish towels), sheets, bath towels) together with swatches of technical stains representing greasy stains, hydrophilic (bleachable) stains and hydrophobic stains. The greasy stains were lipstick, make-up, boot-polish, eye-shadow, and dirty motor oil, all painted onto cotton and aged for two months. The hdrophilic (bleachable) stains were tea, wine, and coffee, all boiled onto cotton, and curry and blackberry, painted on and similarly aged. The hydrophobic stains, painted on and aged similarly, were ragu sauce, tomato paste and siciliana sauce. In addition a number of naturally soiled articles were split into two halves, one of which was washed using the TAED-containing product while the other was washed in a product containing either PAG or TAG-1-10.

The detergent product had the following composition in weight percent.

| Linear Sodium $C_{11.8}$ alkylbenzenesulfonate | 6.9 |
|---|---|
| Sodium Tallow alkyl sulfate | 2.3 |
| Dobonal 45E7 nonionic | 3.25 |
| Tallow alcohol ethoxylate | 1.45 |
| Sodium silicate ($SiO_2:Na_2O = 2:1$) | 3.50 |
| Sodium perborate tetrahydrate | 18.25 |
| Sodium zeolite A | 22.3 |
| DETPMP* | 0.20 |
| Maleic anhydride/acrylic acid copolymer | 3.50 |
| Sodium carbonate | 16.50 |
| Trisodium citrate | 8.0 |
| Optical brightener | 0.25 |
| Carboxymethylcellulose | 0.50 |
| Suds suppressor | 0.45 |
| Moisture & miscellaneous | 8.30 |

*DETPMP = diethylenetriaminepentakis(methylenephosphonic acid)

105 g of the above product and a predetermined level of bleach activator were added to the machine using an Ari-elator® dispensing device except in the case of the TAG-1-10 where the activator was predissolved in methanol and added via the detergent compartment of the dispenser drawer. In the washing liquor, the activator concentrations were 1.3 mM (TAG-1-10), 1.3 mM (PAG), and 2.0 mM (TAED), respectively.

After washing the fabrics were dried in a rotary tumble dryer and the technical stain swatches and split items were assessed for stain removal by an expert panel using a paired comparison technique.

The results are shown in Scheffe panel score units normalised to TAED=0.

|  | P.S.U | | | |
|---|---|---|---|---|
|  | Greasy | Bleachable | Hydrophobic | Split item |
| TAED | 0 | 0 | 0 | 0 |
| PAG | −0.23 | 0.36 | 0.24 | −0.08 |
| TAG-1-10 | 0.67 | −0.21 | 0.84 | 0.47 |

It can be seen that the composition incorporating TAG-1-10 bleach activator demonstrates stain removal benefits across a wide variety of soils.

What is claimed is:

1. A bleaching detergent composition comprising a source of hydrogen peroxide and a compound of formula (I)

(A—CO—) (R'—CO—)$_n$X          (I)

wherein

X is an aldohexose sugar moiety;

A—CO is a $C_8$–$C_{12}$ straight or branched, saturated or unsaturated acyl group attached through an ester bond to the anomeric carbon atom of the sugar moiety;

R'—CO is acetyl attached through an ester bond; and n is 4;

wherein the molar ratio of the source of hydrogen peroxide to the compound is in the range of 1:10 to 20:1.

2. The composition according to claim 1, wherein X is glucose.

3. The composition according to claim 2, wherein A—CO is selected from the group consisting of octanoyl, nonanoyl, decanoyl, undecanoyl, and dodecanoyl.

* * * * *